United States Patent
Lin et al.

(10) Patent No.: US 10,881,621 B2
(45) Date of Patent: Jan. 5, 2021

(54) SINTERED FERROUS AMINO ACID PARTICLES AND USE OF THE SAME AGAINST A VIRUS

(71) Applicant: Profeat Biotechnology Co., Ltd., Taoyuan (TW)

(72) Inventors: Tsun-Yuan Lin, Taoyuan (TW); Mu-Kuei Chen, Taoyuan (TW); Kai-Ting Wang, Taoyuan (TW); Hsun-Jin Jan, Taoyuan (TW)

(73) Assignee: PROFEAT BIOTECHNOLOGY CO., LTD., Taoyuan (TW)

( * ) Notice: Subject to any disclaimer, the term of this patent is extended or adjusted under 35 U.S.C. 154(b) by 0 days.

(21) Appl. No.: 16/527,648

(22) Filed: Jul. 31, 2019

(65) Prior Publication Data

US 2019/0358168 A1 Nov. 28, 2019

Related U.S. Application Data

(62) Division of application No. 16/223,426, filed on Dec. 18, 2018.

(60) Provisional application No. 62/639,064, filed on Mar. 6, 2018.

(51) Int. Cl.
| | | |
|---|---|---|
| *A61K 9/51* | (2006.01) | |
| *A61K 31/295* | (2006.01) | |
| *A61P 31/16* | (2006.01) | |
| *A61P 31/14* | (2006.01) | |
| *A61K 9/00* | (2006.01) | |

(52) U.S. Cl.
CPC .............. *A61K 9/51* (2013.01); *A61K 9/0053* (2013.01); *A61K 31/295* (2013.01); *A61P 31/14* (2018.01); *A61P 31/16* (2018.01)

(58) Field of Classification Search
None
See application file for complete search history.

(56) References Cited

U.S. PATENT DOCUMENTS

| | | |
|---|---|---|
| 2015/0065569 A1 | 3/2015 | Lin et al. |
| 2017/0007568 A1 | 1/2017 | Lin et al. |
| 2017/0224727 A1* | 8/2017 | Lin ...................... A61K 31/198 |
| 2019/0274967 A1 | 9/2019 | Lin et al. |
| 2020/0138726 A1 | 5/2020 | Lin et al. |

FOREIGN PATENT DOCUMENTS

| | | |
|---|---|---|
| TW | I287856 B | 3/2018 |

OTHER PUBLICATIONS

Demetrio et al (Materials Research, 2013, 16(5), 1030-1038). (Year: 2013).*
Saif et al, Pork Gateway, Aug. 29, 2013 (Year: 2013).*
Fenner's Veterinary Virology (Year: 2011).*
The Center for Food Security and Public Health (Year: 2009).*
The Winn Feline Foundation (Year: 2017).*

* cited by examiner

*Primary Examiner* — Celeste A Roney
(74) *Attorney, Agent, or Firm* — Hamre, Schumann, Mueller & Larson, P.C.

(57) ABSTRACT

A composition includes sintered ferrous amino acid particles prepared by sintering a ferrous amino acid chelate which includes ferrous ions and an amino acid. The sintered ferrous amino acid particles have an average particle size ranging from 500 to 2600 nm and a weight average molecular weight ranging from 1,500 Dalton to 600,000 Dalton. Also disclosed herein are a method for inhibiting and/or killing a virus in a subject and applications of such method. The method includes administering to the subject the composition.

3 Claims, No Drawings

SINTERED FERROUS AMINO ACID PARTICLES AND USE OF THE SAME AGAINST A VIRUS

CROSS-REFERENCE TO RELATED APPLICATION

This application is a divisional application of U.S. patent application Ser. No. 16/223,426 (filed on Dec. 18, 2018), which claims priority of U.S. Provisional Patent Application No. 62/639,064 (filed on Mar. 6, 2018). This application claims the benefits and priority of all these prior applications and incorporates by reference the contents of these prior applications in their entirety.

FIELD

The disclosure relates to a composition including sintered ferrous amino acid particles, and a method for inhibiting and/or killing a virus using the composition, as well as applications thereof.

BACKGROUND

The applicant's US Patent Application Publication No. 2017/0224727 A1 has disclosed a ferrous amino acid chelate, which is capable of stably passing through stomach, and which is effective in controlling body weight and enhancing lipid metabolism and lipolysis. In addition, the ferrous amino acid chelate can also be used in the treatment of cancer and diabetes, as well as to reduce the production of lactic acid by cancer cells, as disclosed in the applicant's previous patent applications and patent, including US Patent Application Publication Nos. 2015/0065569 A1 and 2017/0007568 A1 and Taiwanese Invention Patent No. 1587856. These patent applications and patent are hereby incorporated by reference in their entirety.

Porcine epidemic diarrhea virus (PEDV) is a coronavirus that infects the cells lining the small intestine of a pig, causing porcine epidemic diarrhea, a condition of severe diarrhea and dehydration. Older hogs mostly get sick and lose weight after being infected, whereas newborn piglets usually die within five days of contracting the virus. PEDV has a substantial economic burden given that it is highly infectious, resulting in significant morbidity and mortality in piglets.

Viral respiratory diseases are also problematic to swine. Among such viruses, porcine reproductive and respiratory syndrome virus (PRRSV) and swine influenza virus (SIV) are the two main known contributors to lung infectious diseases, and can take effect alone or in combination. Porcine reproductive and respiratory syndrome virus causes porcine reproductive and respiratory syndrome (PRRS), also known as blue-ear pig disease, which causes reproductive failure in breeding stock and respiratory tract illness in young pigs. Swine influenza virus (SIV) causes swine influenza, an acute infectious respiratory disease in pigs, which is characterized by sudden onset, cough, dyspnea, fever and rapid prognosis. Swine influenza has high incidence during autumn and winter though it can be transmitted all year long. Therefore, there is a need to develop an effective and efficient method of killing the aforesaid infectious viruses.

The applicant has surprisingly found that the sintered particles obtained from the ferrous amino acid chelate is effective in inhibiting and/or eliminating a virus, and hence opines that such particles can be used to inhibit and/or eliminate a virus, particularly a porcine virus.

SUMMARY

Accordingly, the present disclosure provides a composition including sintered ferrous amino acid particles, which are prepared by sintering a ferrous amino acid chelate including ferrous ions and an amino acid. The sintered ferrous amino acid particles have an average particle size ranging from 500 to 2600 nm and a weight average molecular weight ranging from 1,500 Dalton to 600,000 Dalton.

The present disclosure also provides a method for inhibiting and/or killing a virus in a subject, which includes administering to the subject the aforementioned composition.

DETAILED DESCRIPTION

Unless defined otherwise, all technical and scientific terms used herein have the meaning commonly understood by a person skilled in the art to which the present disclosure belongs.

One skilled in the art will recognize many methods and materials similar or equivalent to those described herein, which could be used in the practice of the present disclosure. Indeed, the present disclosure is in no way limited to the methods and materials described. For clarity, the following definitions are used herein.

The present disclosure provides a composition including sintered ferrous amino acid particles, which are prepared by sintering a ferrous amino acid chelate including ferrous ions and an amino acid. The sintered ferrous amino acid particles have an average particle size ranging from 500 to 2600 nm and a weight average molecular weight ranging from 1,500 Dalton to 600,000 Dalton.

In certain embodiments, the sintered ferrous amino acid particles have a weight average molecular weight ranging from 1,500 Dalton to 15,000 Dalton. In other embodiments, the sintered ferrous amino acid particles have a weight average molecular weight ranging from 400,000 Dalton to 550,000 Dalton. In an exemplary embodiment, the sintered ferrous amino acid particles have a weight average molecular weight of about 550,000 Dalton.

According to this disclosure, the chelating ratio of the ferrous ions to the amino acid in the ferrous amino acid chelate ranges from 1:1 to 1:4. In certain embodiments, the chelating ratio of the ferrous ions to the amino acid in the ferrous amino acid chelate ranges from 1:1.5 and 1:2.5.

The process for preparing the ferrous amino acid chelate has been disclosed in, e.g. US 2017/0224727 A1, and includes the steps of mixing a ferrous compound with an amino acid under heating. In certain embodiments, the mixing step may be conducted at a temperature ranging from 60° C. to 90° C. In certain embodiments, the mixing step may be conducted for 8 hours to 48 hours.

According to the disclosure, the weight ratio of the ferrous compound and the amino acid used in the preparation process is between 1:1.2 and 1:1.5. In an embodiment of this disclosure, the weight ratio of the ferrous compound and the amino acid is 1:1.3.

In certain embodiments, the ferrous compound may be ferrous sulfate, ferrous chloride, ferrous pyrophosphate, or the combinations thereof.

In certain embodiments, the amino acid may be glycine. That is, the ferrous amino acid chelate may be a ferrous glycinate chelate.

The present disclosure also provides a method for inhibiting and/or killing a virus in a subject, which includes administering to the subject the aforementioned composition.

Examples of the virus suitable for use in this disclosure include, but are not limited to, porcine epidemic diarrhea virus, porcine respiratory and reproductive syndrome virus, influenza virus (such as swine influenza virus, canine influenza virus, equine influenza virus, avian influenza virus, etc.), transmissible gastroenteritis coronavirus, feline coronavirus, canine coronavirus, equine arteritis virus, and combinations thereof.

The composition according to this disclosure may be prepared in the form of a pharmaceutical composition or a food composition.

If the composition is prepared in the form of the pharmaceutical composition, the composition may further include a pharmaceutically acceptable carrier, and may be made into a dosage form suitable for oral administration using technology well-known to those skilled in the art. Examples of the dosage form include, but are not limited to, solution, suspension, emulsion, powder, tablet, pill, syrup, lozenge, troche, chewing gum, capsule, slurry and the like.

Examples of the pharmaceutically acceptable carrier suitable for use in this disclosure may include, but are not limited to, solvent, emulsifier, suspending agents, decomposers, binding agents, excipients, stabilizing agents, chelating agents, diluents, gelling agents, preservatives, lubricants, absorption delaying agents, liposomes, and combinations thereof.

The composition according to this disclosure may be in the form of a food additive (an exemplary example of the food composition), which can be added into an edible material to prepare a food product for human or animal consumption. Examples of the food product according to this disclosure may include, but are not limited to: fluid milk products, e.g., milk and concentrated milk; fermented milk, e.g., yogurt, sour milk and frozen yogurt; milk powder; ice cream; cream cheeses; dry cheeses; soybean milk; fermented soybean milk; vegetable-fruit juices; fruit juices; sports drinks; confectionery; jelly; candies; health foods; animal feeds; and dietary supplements.

As used herein, the term "subject" refers to any animal of interest, such as humans, monkeys, cows, sheeps, horses, pigs, goats, dogs, cats, mice and rats. In certain embodiments, the subject may be a human. In other embodiments, the subject may be a pig.

The dosage and the frequency of administration of the composition according to this disclosure may vary depending on the following factors: the severity of the virus to be inhibited and/or killed, and the weight, age, physical condition and response of the subject to be treated. For instance, the daily dosage of the composition according to this disclosure may be 12 to 36 mg per kg of the body weight, and may be administered in a single dose or in several doses.

This disclosure will be further described by way of the following examples. However, it should be understood that the following examples are solely intended for the purpose of illustration and should not be construed as limiting the disclosure in practice.

EXAMPLES

General Experimental Materials:
1. Pharmaceutical Composition A1:

Pharmaceutical Composition A1 (batch number: F171001; production date: 2017 Oct. 5), which contained sintered ferrous amino acid particles, was in the form of lyophilized powder, and was produced by Taiwan Bioligand Co., Ltd.

Specifically, ferrous sulfate was mixed with glycine (above 98% purity) in a weight ratio of 1:1.3, followed by heating from 60° C. to 90° C. for 8 hours to 48 hours to obtain ferrous amino acid chelates with a chelating ratio of the ferrous irons to the amino acid ranging from 1:1 to 1:4. The ferrous amino acid chelates were then sintered at a temperature ranging from 200° C. to 240° C. to obtain the sintered ferrous amino acid particles.

The average particle size of the sintered ferrous amino acid particles measured in water by dynamic light scattering (DLS) on Beckman Coulter N5 Submicron Particle Size Analyzer was 1465.90±132.29 nm.

The number-average molecular weight (Mn), weight-average molecular weight (Mw), peak molecular weight (MP) and polydispersity (PDI) of the sintered ferrous amino acid particles dissolved in water, determined by gel permeation chromatography using Waters Alliance 2695 System, were 68188 Dalton, 525538 Dalton, 286426 Dalton and 7.707205, respectively.

Pharmaceutical Composition A1 was dissolved in sterile purified water to prepare a stock solution having a concentration of 250 mg/mL for use in the following examples.

2. Virus:

Porcine epidemic diarrhea virus (PEDV), porcine respiratory and reproductive syndrome virus (PRRSV) and swine influenza virus (SIV) were obtained from Shanghai Academy of Agricultural Sciences (SAAS), China.

3. Host Cells for Propagating Viruses:

Vero cells (ATCC CCL-81) for propagating PEDV, MARC 145 cells (ATCC CRL-12231) for propagating PRRSV, and MDCK cells (ATCC CCL-34) for propagating SIV were obtained from Shanghai Academy of Agricultural Sciences (SAAS), China.

Example 1. Effect of Pharmaceutical Composition A1 on Porcine Epidemic Diarrhea Virus (PEDV)

Experimental Procedures:

A. Pretreatment of Host Cells with Pharmaceutical Composition A1 Before Virus Inoculation, and Subsequent Virus Inoculation of Pretreated Host Cells with PEDV Well grown Vero cells, after detachment, were subjected to dilution using a DMED medium so as to reach a cell concentration of $10^6$ cell/mL. To each of aliquot portions of the resulting cell suspension containing the DMED medium was added a suitable amount of the stock solution containing Pharmaceutical Composition A1, so that cell suspensions respectively having final concentrations of Pharmaceutical Composition A1 being 1000 μg/mL, 500 μg/mL, and 100 μg/mL were obtained. On a 24-well cell cultivation plate, the cells treated with Pharmaceutical Composition A1 at a respective concentration were seeded into 6 wells, and a cell control (without the treatment of the stock solution containing Pharmaceutical Composition A1) was seeded as well. The cell cultivation plate was placed at 37° C. for 24 hours of incubation, and was then retrieved to remove the medium via suction. The cells were washed thrice using a sterile PBS solution.

A PEDV solution was diluted at a ratio of 1:200. 100 μL of the resulting diluted virus solution was inoculated into each well. Virus adsorption was conducted at 37° C. for 1 hour. Afterward, the virus solution was removed via suction. 100 μL of a DMEM complete medium was added into each well, followed by incubation at 37° C. The cytopathic effect was observed. Each of the virus-containing media was collected at 96 hour so as to determine the $TCID_{50}$ (50% tissue culture infection dose) of the virus.

B. Virus Inoculation of Host Cells with Pharmaceutical Composition A1-Treated PEDV Well grown Vero cells, after detachment, were subjected to dilution so as to reach a cell concentration of $10^6$ cell/mL, followed by cell plating onto a 24-well cell cultivation plate. Incubation was conducted at 37° C. for 24 hours.

A sterile PBS solution was used to dilute PEDV at a ratio of 1:200. To each of aliquot portions of the resulting diluted PEDV solution was added a suitable amount of the stock solution containing Pharmaceutical Composition A1, so that Pharmaceutical Composition A1-treated PEDV solutions respectively having final concentrations of Pharmaceutical Composition A1 being 1000 μg/mL, 500 μg/mL, and 100 μg/mL were obtained. The treatment was allowed to proceed at 37° C. for 1 hour.

Subsequently, the Pharmaceutical Composition A1-treated PEDV solutions were inoculated into the 24-well cell cultivation plate. Specifically, a respective one of the Pharmaceutical Composition A1-treated PEDV solutions was inoculated into 6 wells, and each well received 100 μL of the respective Pharmaceutical Composition A1-treated PEDV solution.

In addition, a cell control was inoculated virus without the treatment of Pharmaceutical Composition A1.

The cell cultivation plate was placed at 37° C. for incubation. The cytopathic effect was observed. Each of the virus-containing solutions was collected at 96 hour so as to determine the $TCID_{50}$ of the virus.

Results:

A. Pretreatment of Host Cells with Pharmaceutical Composition A1 Before Virus Inoculation, and Subsequent Virus Inoculation of Pretreated Host Cells with PEDV The cytopathic effect observed and the $TCID_{50}$ of the virus determined in the Vero host cells pretreated with Pharmaceutical Composition A1 are shown in Tables 1 and 2 below, respectively.

TABLE 1

Degree of cytopathic effect observed

| Concentration of Pharmaceutical Composition A1 | 1st well | 2nd well | 3rd well | 4th well |
| --- | --- | --- | --- | --- |
| 1000 μg/mL | ++++ | ++++ | ++++ | ++++ |
| 500 μg/mL | ++++ | ++++ | ++++ | ++++ |
| 100 μg/mL | ++++ | ++++ | ++++ | ++++ |
| 0 μg/mL | ++++ | ++++ | ++++ | ++++ |

TABLE 2

$TCID_{50}$ determined

| Concentration of Pharmaceutical Composition A1 | $TCID_{50}$ |
| --- | --- |
| 1000 μg/mL | $10^{-1}$/0.1 mL |
| 500 μg/mL | $10^{-1.6667}$/0.1 mL |
| 100 μg/mL | $10^{-2.2241}$/0.1 mL |
| 0 μg/mL | $10^{-6.3441}$/0.1 mL |

As shown in Table 2, the higher the concentration of Pharmaceutical Composition A1, the higher the $TCID_{50}$ determined was, indicating that a pretreatment with a suitable concentration of Pharmaceutical Composition A1 can lead to inhibition against propagation of PEDV in the host cells.

B. Virus Inoculation of Host Cells with Pharmaceutical Composition A1-Treated PEDV The cytopathic effect observed and the $TCID_{50}$ of the Pharmaceutical Composition A1-treated PEDV determined in the host cells are shown in Tables 3 and 4 below, respectively.

TABLE 3

Degree of cytopathic effect observed

| Concentration of Pharmaceutical Composition A1 | 1st well | 2nd well | 3rd well | 4th well |
| --- | --- | --- | --- | --- |
| 1000 μg/mL | +++ | +++ | ++ | ++ |
| 500 μg/mL | ++ | ++ | + | ++ |
| 100 μg/mL | ++ | ++ | ++ | + |
| 0 μg/mL | ++++ | ++++ | ++++ | ++++ |

TABLE 4

$TCID_{50}$ determined

| Concentration of Pharmaceutical Composition A1 | $TCID_{50}$ |
| --- | --- |
| 1000 μg/mL | $10^{-3.5714}$/0.1 mL |
| 500 μg/mL | $10^{-4.4099}$/0.1 mL |
| 100 μg/mL | $10^{-5.4099}$/0.1 mL |
| 0 μg/mL | $10^{-6.3441}$/0.1 mL |

As shown in Table 3, the treatment with Pharmaceutical Composition A1 reduced the degree of cytopathic effect, manifesting that Pharmaceutical Composition A1 is effective in inhibiting and/or killing a virus. In particular, when either 500 μg/mL or 100 μg/mL of Pharmaceutical Composition A1 was applied, the cytopathic effect was significantly delayed, and a significantly lower degree of cytopathic effect was observed.

As shown in Table 4, the higher the concentration of Pharmaceutical Composition A1, the higher the $TCID_{50}$ was, indicating that a treatment with a suitable concentration of Pharmaceutical Composition A1 can lead to inhibition against propagation of PEDV in the host cells.

Example 2. Effect of Pharmaceutical Composition A1 on Porcine Respiratory and Reproductive Syndrome Virus (PRRSV)

Experimental Procedures:

A. Pretreatment of Host Cells with Pharmaceutical Composition A1 Before Virus Inoculation, and Subsequent Virus Inoculation of Pretreated Host Cells with PRRSV On a 24-well cell cultivation plate, MARC 145 host cells pretreated with Pharmaceutical Composition A1 at a respective concentration of 1000 μg/mL, 500 μg/mL, and 100 μg/mL, which were prepared according to the procedure described in section A of Example 1, were seeded into 6 wells, and a cell control (without the treatment of Pharmaceutical Composition A1) was seeded as well. The cell cultivation plate was placed at 37° C. for 24 hours of incubation, and was then retrieved to remove the medium via suction. The cells were washed thrice using a sterile PBS solution.

A PRRSV solution was diluted at a ratio of 1:200. 100 μL of the resulting diluted virus solution was inoculated into each well. Virus adsorption was conducted at 37° C. for 1 hour. Afterward, the virus solution was removed via suction. 100 μL of a DMEM complete medium was added into each well, followed by incubation at 37° C. Each of the virus-containing media was collected at 92 hour so as to determine the virus contents in the host cells pretreated with different concentrations of Pharmaceutical Composition A1, relative to the cell control.

B. Virus Inoculation of Host Cells with Pharmaceutical Composition A1-Treated PRRSV Pharmaceutical Composition A1 was dissolved in sterile purified water to prepare a stock solution having a concentration of 250 mg/mL. Well grown MRAC 145 cells, after detachment, were subjected to dilution so as to reach a cell concentration of $10^6$ cell/mL, followed by cell plating onto a 24-well cell cultivation plate. Incubation was conducted at 37° C. for 24 hours.

Pharmaceutical Composition A1-treated PRRSV solutions respectively having final concentrations of Pharmaceutical Composition A1 being 1000 μg/mL, 500 μg/mL, and 100 μg/mL were prepared according to the procedure described in section B of Example 1.

Subsequently, the Pharmaceutical Composition A1-treated PRRSV solutions were inoculated into the 24-well cell cultivation plate. Specifically, a respective one of the Pharmaceutical Composition A1-treated PRRSV solutions was inoculated into 6 wells, and each well received 100 μL of the respective Pharmaceutical Composition A1-treated PRRSV solution.

In addition, a cell control was inoculated virus without the treatment of Pharmaceutical Composition A1.

The cell cultivation plate was placed at 37° C. for incubation. Each of the virus-containing solutions was collected at 96 hour so as to determine the virus contents in the cells inoculated with different concentrations of Pharmaceutical Composition A1-treated PRRSV solutions, relative to the normal cell control.

Results:

A. Pretreatment of Host Cells with Pharmaceutical Composition A1 Before Virus Inoculation, and Subsequent Virus Inoculation of Pretreated Host Cells with PRRSV The virus content determined in the host cells pretreated with Pharmaceutical Composition A1 is shown in Table 5.

TABLE 5

Virus content determined in the host cells

| Concentration of Pharmaceutical Composition A1 | Virus content (relative to the cell control) |
|---|---|
| 1000 μg/mL | 0.322 |
| 500 μg/mL | 0.664 |
| 100 μg/mL | 0.876 |
| 0 μg/mL | 1 |

As shown in Table 5, the higher the concentration of Pharmaceutical Composition A1, the lower the virus content was, indicating that a pretreatment with a suitable concentration of Pharmaceutical Composition A1 can lead to inhibition against propagation of PRRSV in the host cells.

B. Virus Inoculation of Host Cells with Pharmaceutical Composition A1-Treated PRRSV The virus content determined in the host cells inoculated with Pharmaceutical Composition A1-treated PRRSV is shown in Table 6 below.

TABLE 6

Virus content determined in the host cells

| Concentration of Pharmaceutical Composition A1 | Virus content (relative to the cell control) |
|---|---|
| 1000 μg/mL | 0.681 |
| 500 μg/mL | 0.77 |
| 100 μg/mL | 0.96 |
| 0 μg/mL | 1 |

As shown in Table 6, the treatment with Pharmaceutical Composition A1 reduced the virus content in the host cells, manifesting that Pharmaceutical Composition A1 is effective in inhibiting and/or killing a virus. In particular, the higher the concentration of Pharmaceutical Composition A1, the lower the virus content was, indicating that a treatment with a suitable concentration of Pharmaceutical Composition A1 can lead to inhibition against propagation of PRRSV in the host cells.

Example 3. Effect of Pharmaceutical Composition A1 on Swine Influenza Virus (SIV)

Experimental Procedures:

A. Pretreatment of Host Cells with Pharmaceutical Composition A1 Before Virus Inoculation, and Subsequent Virus Inoculation of Pretreated Host Cells with SIV On a 24-well cell cultivation plate, MDCK cells treated with Pharmaceutical Composition A1 at a respective concentration of 1000 μg/mL, 500 μg/mL, and 100 μg/mL, which were prepared according to the procedure described in section A of Example 1, were seeded into 6 wells, and a cell control (without the treatment of Pharmaceutical Composition A1) was seeded as well. The cell cultivation plate was placed at 37° C. for 24 hours of incubation, and was then retrieved to remove the medium via suction. The cells were washed thrice using a sterile PBS solution.

A SIV solution was diluted at a ratio of 1:200. 100 μL of the resulting diluted virus solution was inoculated into each well. Virus adsorption was conducted at 37° C. for 1 hour. Afterward, the virus solution was removed via suction. 100 μL of a serum-containing complete medium was added into each well, followed by incubation at 37° C. Each of the virus-containing media was collected at 72 hour so as to determine the $TCID_{50}$ of the virus using the Reed-Muench method.

B. Virus Inoculation of Host Cells with Pharmaceutical Composition A1-Treated SIV Pharmaceutical Composition A1 was dissolved in sterile purified water to prepare a stock solution having a concentration of 250 mg/mL. Well grown MDCK cells, after detachment, were subjected to dilution so as to reach a cell concentration of 10 cell/mL, followed by cell plating onto a 24-well cell cultivation plate. Incubation was conducted at 37° C. for 24 hours.

Pharmaceutical Composition A1-treated SIV solutions respectively having final concentrations of Pharmaceutical Composition A1 being 1000 μg/mL, 500 μg/mL, and 100 μg/mL were prepared according to the procedure described in section B of Example 1.

Subsequently, the Pharmaceutical Composition A1-treated SIV solutions were inoculated into the 24-well cell cultivation plate. Specifically, a respective one of the Pharmaceutical Composition A1-treated SIV solutions was inoculated into 6 wells, and each well received 100 μL of the respective Pharmaceutical Composition A1-treated SIV solution. In addition, a cell control was inoculated virus without the treatment of Pharmaceutical Composition A1.

The cell cultivation plate was placed at 37° C. for incubation. Each of the virus-containing solution was collected at 72 hour so as to determine the $TCID_{50}$ of the virus using the Reed-Muench method.

Results:

A. Pretreatment of Host Cells with Pharmaceutical Composition A1 Before Virus Inoculation, and Subsequent Virus Inoculation of Pretreated Host Cells with SIV The $TCID_{50}$ of the virus determined in the host cells pretreated with Pharmaceutical Composition A1 is shown in Table 7 below.

TABLE 7

$TCID_{50}$ determined determined in the host cells

| Concentration of Pharmaceutical Composition A1 | $TCID_{50}$ |
|---|---|
| 1000 μg/mL | $10^{-2.7}$/0.1 mL |
| 500 μg/mL | $10^{-3.18}$/0.1 mL |
| 100 μg/mL | $10^{-3.39}$/0.1 mL |
| 0 μg/mL | $10^{-4.88}$/0.1 mL |

As shown in Table 7, the higher the concentration of Pharmaceutical Composition A1, the higher the $TCID_{50}$ was, indicating that a pretreatment with a suitable concentration of Pharmaceutical Composition A1 can lead to inhibition against propagation of SIV in the host cells.

B. Virus Inoculation of Host Cells with Pharmaceutical Composition A1-Treated SIV The $TCID_{50}$ of the Pharmaceutical Composition A1-treated SIV determined in the host cells is shown in Table 8 below.

TABLE 8

$TCID_{50}$ determined in the host cells

| Concentration of Pharmaceutical Composition A1 | $TCID_{50}$ |
|---|---|
| 1000 μg/mL | $10^{-2.28}$/0.1 mL |
| 500 μg/mL | $10^{-3.45}$/0.1 mL |
| 100 μg/mL | $10^{-3.59}$/0.1 mL |
| 0 μg/mL | $10^{-4.88}$/0.1 mL |

As shown in Table 8, the treatment with Pharmaceutical Composition A1 reduced the virus propagation, manifesting that Pharmaceutical Composition A1 is effective in inhibiting and/or killing a virus. In particular, the higher the concentration of Pharmaceutical Composition A1, the higher the $TCID_{50}$ was, indicating that a treatment with a suitable concentration of Pharmaceutical Composition A1 can lead to inhibition against propagation of SIV in the host cells.

Based on the above results, the applicant surprisingly found that the sintered ferrous amino acid particles of this disclosure obtained from a ferrous amino acid chelate can inhibit and/or kill a virus, thereby significantly reducing the virus propagation in host cells.

All patents and literature references cited in the present specification as well as the references described therein, are hereby incorporated by reference in their entirety. In case of conflict, the present description, including definitions, will prevail.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for inhibiting and/or killing a virus in a subject, the method comprising:
   administering to the subject infected with the virus a composition including sintered ferrous amino acid particles prepared by sintering a ferrous amino acid chelate comprising a ferrous ion and an amino acid, the sintered ferrous amino acid particles having an average particle size ranging from 500 to 2600 nm and having a weight average molecular weight ranging from 1,500 Dalton to 600,000 Dalton,
   wherein the virus is selected from the group consisting of porcine epidemic diarrhea virus, porcine respiratory and reproductive syndrome virus, swine influenza virus, and combinations thereof.

2. The method of claim 1, wherein the composition is orally administered.

3. The method of claim 1, wherein the composition is a pharmaceutical composition.

* * * * *